United States Patent [19]
Gilis et al.

[11] Patent Number: 6,030,988
[45] Date of Patent: *Feb. 29, 2000

[54] IMMEDIATE RELEASE PH-INDEPENDENT SOLID DOSAGE FORM OF CISAPRIDE

[75] Inventors: Paul Marie Victor Gilis, Beerse; Guido Franciscus Smans, Lille; Guido Jozef Maria Gijs, Arendonk, all of Belgium

[73] Assignee: Janssen Pharmaceutica, N.V., Beerse, Belgium

[ * ] Notice: This patent issued on a continued prosecution application filed under 37 CFR 1.53(d), and is subject to the twenty year patent term provisions of 35 U.S.C. 154(a)(2).

[21] Appl. No.: 08/821,151

[22] Filed: Mar. 20, 1997

[30] Foreign Application Priority Data

Apr. 23, 1996 [EP] European Pat. Off. .............. 96201078

[51] Int. Cl.[7] .................................................. A61K 31/445
[52] U.S. Cl. .............................................. 514/327
[58] Field of Search ............................................. 514/327

[56] References Cited

U.S. PATENT DOCUMENTS 4,962,115  10/1990  Van Daele ............................. 514/326

FOREIGN PATENT DOCUMENTS

| 0670160 | 9/1995 | European Pat. Off. . |
|---|---|---|
| 94/01112 | 1/1994 | WIPO . |
| WO 94/01111 | 1/1994 | WIPO . |
| WO 95/01803 | 1/1995 | WIPO . |
| WO 95/34284 | 12/1995 | WIPO . |
| WO 96/14070 | 5/1996 | WIPO . |

*Primary Examiner*—Rebecca Cook
*Attorney, Agent, or Firm*—Ellen Ciambrone Coletti

[57] ABSTRACT

The present invention concerns oral dosage forms of some particular salts of cisapride, more particularly cisapride-(L)-tartrate, cisapride-(D)-tartrate, cisapride-sulfate, or cisapride citrate, which avoid drugfood interaction and which allow comedication of agents that increase the pH of the stomach. The invention particularly relates to solid oral dosage forms suitable for rapid dissolution. The present invention also concerns tablets which can be prepared via direct compression.

11 Claims, No Drawings

IMMEDIATE RELEASE PH-INDEPENDENT SOLID DOSAGE FORM OF CISAPRIDE

The present invention concerns solid dosage forms of particular salts of cisapride, more particularly cisapride-(L)-tartrate, cisapride-(D)-tartrate, cisapride-sulfate, or cisapride citrate, which avoid drugfood interaction and which allow co-medication of agents that increase the pH of the stomach. The invention particularly relates to solid oral dosage forms suitable for rapid disintegration and dissolution. The present invention also concerns tablets which can be prepared via direct compression.

INTRODUCTION

In general, it is known that the absorption and bioavailability of any particular therapeutic agent can be affected by numerous factors when dosed orally. Such factors include the presence of food in the gastrointestinal (GI) tract because, in general, the gastric residence time of a drug is usually significantly longer in the presence of food than in the fasted state. If the bioavailability of a drug is affected beyond a certain point due to the presence of food in the GI tract, the drug is said to exhibit a "food effect" or show a drugfood interaction. The risk involved with taking drugs exhibiting a food-effect derives from the fact that absorption into the bloodstream may be adversely affected by not taking the drug on the correct point in time so that the patient risks insufficient absorption to remedy the condition for which the drug was administered.

European Patent No 0,076,530 discloses the gastroprokinetic agent cisapride and compositions thereof. Cisapride has the following structural formula:

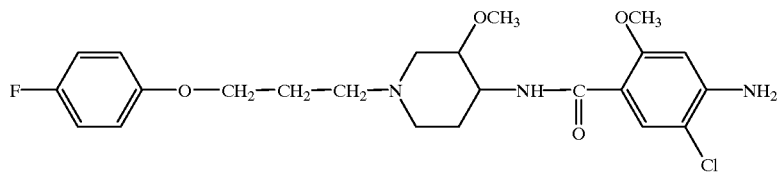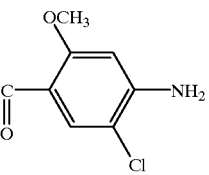

The systematic chemical name of cisapride is cis-4-amino-5-chloro-N-[1-[3-(4-fluoro-phenoxy)propyl]-3-methoxy4-piperidinyl]-2-methoxybenzamide. Cisapride is a racemic mixture of two enantiomers. Cisapride has excellent gastrointestinal motility stimulating properties and is reported to be devoid of antidopaminergic activity. Its utility in a variety of gastro-intestinal disorders has already been reported extensively. It is currently being marketed as a medicine to treat gastro-oesophageal reflux disorders, inter alia oesophagitis, gastroparesis, negative upper digestive discomfort and intestinal pseudo-obstruction. Cisapride monohydrate is currently commercially available as tablets, suspension and granules under registered tradenames, such as PREPULSID™, PROPULSID™, PROPULSIN™, ACENALIN™, ALIMIX™ (this list is not comprehensive).

Cisapride in its monohydrate form has a pH-dependent solubility and dissolution profile. Hence the bioavailability of cisapride or cisapride monohydrate is pH dependent. Cisapride monohydrate has a low solubility and low dissolution when present in a neutral or basic environment. Therefore, the information leaflet of cisapride monohydrate mentions that the drug should be taken 15 to 30 minutes before meals. The rationale being that the solid dosage form comprising cisapride monohydrate arrives in a more or less empty stomach, where the pH is reasonably low and hence the cisapride can dissolve. Subsequently, when the patient takes a meal 15 to 30 minutes after the solid oral dosage form was administered, the solid dosage form remains somewhat longer in the acid environment of the stomach. Once cisapride monohydrate enters the more or less neutral environment of the gut the solubility of cisapride monohydrate decreases rapidly.

Consequently, cisapride monohydrate shows a food effect, which can be expressed as the ratio between the AUC in fed state over AUC in fasted state. (AUC is the abbreviation of Area Under the Curve, which is an indication of the amount of active ingredient that is present in the blood). The ratio for cisapride monohydrate of AUC in fed state over AUC in fasted state is about 1.35 (p>0.01). A drug showing no food effect would have a ratio of 1 (in an ideal case).

Hence, a patient taking cisapride monohydrate has to follow the above described regimen quite strictly in order to create the optimum conditions for high bioavailability of cisapride monohydrate and consequently to maximise the benefit from the drug taken. Patients do not always have the necessary discipline to take their medication at the optimum point in time. Consequently, a dosage form that would make the bioavailability independent of the meal (or from any other event for that matter) would mean a serious improvement over the prior art oral dosage forms of cisapride monohydrate and reduce the extent of variability in absorption between patients.

It would accordingly be useful if cisapride could be administered immediately to patients that feel upcoming pain associated with gastro esophageal reflux, without having to eat 15 to 30 minutes after the administration of cisapride. With the presently available dosage forms of cisapride, the patient would have to eat something in order to obtain maximum absorption of the cisapride monohydrate. In view of the fact that gastro esophageal reflux often occurs during the night and in view of the fact that the oesophagus is causing the pain, it is obvious that the patient is not really inclined to eat anything. Hence, it would be advantageous to have a form of cisapride which can be administered or taken independently from the meal.

There is also a problem associated with pediatric use of cisapride monohydrate. Cisapride monohydrate is prescribed for infants (children up to 1 year). The fact that cisapride monohydrate has to be administered up to 30 minutes before the meal implies that parents often have to wake said children up, administer the cisapride monohydrate and then wait half an hour to feed said children. Said procedure is very unpractical and it would be very interesting to find a form of cisapride which is suitable for administering to infants just before the meal or even after the meal or better still, completely independent of when the meal is taken.

Yet another issue with the present oral dosage forms of cisapride monohydrate is the following. As mentioned above, cisapride is used to treat people having stomach or esophagus problems. Often, these patients receive co-medication to increase the pH of the stomach. Examples of such co-medication are antacids, such as aluminum containing antacids, e.g. Al(OH)$_3$, calcium containing antacids, e.g. CaCO$_3$, or magnesium containing antacids, e.g. Mg(OH)$_2$; H$_2$-antagonists, e.g. cimetidine, ranitidine, famotidine, nizatidine, roxatidine and the like; or proton pump inhibitors, e.g. omeprazole, lansoprazole, rabeprazole. At the moment the preferred comedication prescribes proton pump inhibitors.

PRIOR ART

WO 94/01112 and WO 94/01111, published on Jan. 20, 1994, assigned to Sepracor Inc, disclose very generally methods of using (−)-cisapride respectively (+)-cisapride as well as the therapeutically acceptable salts thereof for the treatment of gastro-esophageal reflux disease and other disorders. In said applications there is no specific mentioning of the use of the presently disclosed salts and the properties thereof. There is also no mentioning of the problem that forms the basis of the present invention. WO 95/34284, published on Dec. 21, 1995, assigned to Gergely, mentions pharmaceutical preparations with a hydrophobic active substance, amongst others cisapride, and an effervescent system, and a process for preparing said preparations. This application only mentions effervescent systems which are totally different from the presently disclosed invention.

EP 670160, published on Sep. 6, 1995, assigned to Gergely, discloses a granular product or tablet containing an effervescent system and an active pharmaceutical substance, as well as a method for its preparation. In example 5 of said document cisapride effervescent tablets are described. Again, in this application only effervescent systems are disclosed which are totally different from the presently disclosed invention.

WO 95/01803, published on Jan. 19, 1995 discloses combinations of H2 antagonists and gastrointestinal motility agents. Said patent application specifically mentions the use of cisapride in said combination. The disadvantage of said prior art combination is that antacids, H2-antagonists and especially proton pump inhibitors can cause a considerable raise in the pH in the stomach. With antacids the pH of the stomach, which is normally between 1 and 1.5, can raise to about 4.5 and with proton pump inhibitors the pH of the stomach can raise to about 6.5. In such an environment cisapride monohydrate does not dissolve quickly enough to give fast appropriate relief.

Our copending application PCT/EP95/04198 discloses a matrix-formulation wherein cisapride-(L)-tartrate is embedded in a mixture of viscous polymers. Said copending application also discloses the preparation of cisapride-(L)-tartrate. In said application it was already disclosed that the salt cisapride-(L)-tartrate is a mixture of the diastereomers [(3R4S)(2R3R)] and [(3S4R)(2R3R)], that crystallize as a double salt in a 1:1 ratio. (This is confirmed by X-ray.) The (3R4S) and (3S4R) refer to the respective enantiomers of cisapride and the (2R3R) refers to the optically pure L-tartrate. It was also shown that formulations containing cisapride-(L)-tartrate released cisapride in a racemic form, i.e. equal amounts of (+)-cisapride and (−)-cisapride or in other words the diastereomeric salt forms (+)-cisapride-(L)-tartrate and (−)-cisapride-(L)-tartrate unexpectedly have equal dissolution rates. Moreover, it was also found that during the preparation of cisapride-(L)-tartrate no enrichment of one of the two diastereomeric salt forms could be detected.

Said prior art matrix formulations, however, do not disintegrate and dissolve as rapidly as is required for the solid oral dosage forms of the present invention. On the contrary, the matrix formulations of the prior art are designed to give a sustained release of cisapride over a much longer period of time.

THE INVENTION

The above mentioned problems and/or disadvantages associated with the prior art formulations are solved by the solid dosage forms comprising a salt of cisapride with an acid selected from sulfuric acid, (L)-tartaric acid, (D)-tartaric acid or citric acid, preferably cisapride-(L)-tartrate suitable for rapid dissolution. The formulations are preferably suitable for rapid disintegration as well as dissolution. The preferred formulations are oral solid dosage forms.

The wording "suitable for rapid dissolution" refers to the fact that from the solid dosage forms of the present invention the active ingredient can dissolve for more than 60% within 1 hour in a pH range from 1 to 7. Said dissolution can be measured according to standard methods described in the European Pharmacoeipea or as set forth in USP test <711> in a USP-2 dissolution apparatus. This latter test is described in US Pharmacopeia XXII, pp 1578–1579.

Unexpectedly we have found that certain salts of cisapride have a better dissolution in artificial gastric juice than others: those salts are the (L)-tartrate, (D)-tartrate, the sulfate and the citrate. Moreover, said salts of cisapride show a dissolution profile which is substantially pH independent. It should be noted that the salt form of cisapride with hydrochloric acid as well as with maleic acid dissolve slower than the cisapride monohydrate itself.

The term "solid oral dosage forms" generally refers to tablets (both swallowable-only and chewable forms) and capsules. Hence, the present composition of salt forms of cisapride may be formulated into tablets, caplets, gelcaps or capsules.

This invention encompasses formulations comprising the salts of cisapride according to the present invention and further comprising a substance which can influence the acidity of the stomach. Said substance can be any medication that increases the pH of the stomach (in other words: renders the stomach more basic). As examples of just medication that increases the pH of the stomach should be mentioned antacids, H2-antagonists or proton pump inhibitors.

The invention also relates to products containing any of the salt forms of cisapride of the present invention, preferably cisapride-(L)-tartrate, and an antacid or an H2-antagonist or especially a proton pump inhibitor as a combined preparation for simultaneous, separate or sequential use in treating gastrointestinal disorders, especially gastro-esophageal reflux related conditions.

The formulations of the present invention may optionally include an anti-flatulent, such as simethicone, alpha-D-galactosidase and the like.

Said products comprising combinations of antacids, H2 antagonists or proton pump inhibitors on the one hand and the cisapride salt forms on the other hand, optionally further combined with an anti flatulent provide the dual action approach to the treatment of gastrointestinal disorders as described in WO 95/01803, i.e. the salt of cisapride as gastrointestinal motility agent offers an enhanced motility while the antacid, the H2-antagonist or the proton pump inhibitor offers a systemic effect of reduced acid production.

The present invention therefore further provides a method of preventing, treating and relieving heartburn, indigestion, sour stomach, overindulgence, gastro esophageal reflux, constipation, dyspepsia and other gastrointestinal disorders, and gastrointestinal disorders, and optionally flatulence, in mammals, including humans, in need of treatment thereof, comprising administering to such organism:

(i) an therapeutically effective amount of an antacid, an H2 antagonist or a proton pump inhibitor, and (ii) a therapeutically effective amount of a salt form of cisapride of the present invention, and optionally (iii) a therapeutically effective amount of an anti-flatulent, in particular simethicone or alpha-D-galactosidase (ADG).

The antacids to be used in the above described combination are commercially available. H2 antagonists such as famotidine, ranitidine and cimetidine are also commercially available under different Tradenames. Proton pump inhibitors, such as, omeprazole, lansoprazole, rabeprazole and the like are either commercially available or known in the art. Simethicone is a well-known and commercially available anti flatulent. Alpha-D-galactosidase ADG is a commercially available enzyme preparation used to hydrolyze indigestible sugars found in beans or bean products. The active ingredients, other than the salts of cisapride are therefore readily commercially available.

The dosages of each of the active ingredients may vary depending upon the severity of the condition and the particular biochemistry and need of the patient. The dosages of the active ingredients may also vary depending upon whether the active ingredients are administered in tablet or liquid form or via some other suitable delivery method. A physician or clinician may readily determine suitable dosages.

The tablets or capsules according to the invention comprise the salt forms of cisapride, preferably cisapride-(L)-tartrate, which are preferably in a microfine or micronized form for some uses. Micronized forms of the salt forms of cisapride, especially cisapride-(L)-tartrate, may be prepared by micronization techniques known in the art, e.g. by milling in appropriate mills and sieving through appropriate sieves.

The specific surface area of said micronized material should at least amount to about $10 \times 10^3$ cm$^2$/g ($1 \times 10^3$ m$^2$/kg), preferably the specific surface area should amount to more than $12 \times 10^3$ cm$^2$/g ($1.2 \times 10^3$ m$^2$/kg), most preferably the specific area should amount to more than $14 \times 10^3$ cm$^2$/g ($1.4 \times 10^3$ m$^2$/kg).

According to this invention the characteristics of the micronized salt forms of cisapride, especially cisapride-(L)-tartrate, expressed in a different way are as follows. At most 50% of the particles may have a diameter larger than 24 μm (i.e. $24 \times 10^{-6}$ m), hence the dl $_{50}$ has a maximum value of 24 μm (dl stands for diameter measured via laser diffraction).

In some cases it may be useful to use coarser material (than the micronized or microfine material) of the presently described salts of cisapride. For instance in the case of direct compressing the tablets comprising the salts of the present invention on an industrial scale. When the active ingredient is too fine there may arise problems when producing tablets via direct compression on industrial (high-speed) machines. When the material is too fine, the tablets show low assay values, which may for example be due to the fact that the micronized material sticks to the walls of containers.

On the other hand when the material is too coarse there may arise a problem with content uniformity, which is a critical parameter. Especially for production of pharmaceutical compositions which is governed by the strict requirements of GMP (Good Manufacturing Practices).

An interesting range of particle size expressed in dl $_{50}$ is from about 10 μm to about 150 μm. A more interesting range is from about 20 μm to 100 μm. For formulations wherein the micronized material is used the preferred dl $_{50}$ is about 24 μm. For formulations wherein the coarser material is used the preferred dl $_{50}$ is about 50 μm.

The solid oral dosage form when in a unit dose form comprises the equivalent of about 0.1 mg to 100 mg of cisapride in it's base form, more particularly are envisaged dosage forms which contain the equivalent of about 5 mg, about 10 mg, and about 20 mg of cisapride in it's base form. This means, for instance for cisapride-(L)-tartrate from about 0.13 mg to about 130 mg cisapride-(L)-tartrate. More particularly dosage forms containing about 6.5 mg, about 13 mg and about 26 mg of cisapride-(L)-tartrate are envisaged.

In view of the fact that the present oral dosage forms are designed to give a fast dissolution of the active ingredient, the excipients of the oral dosage forms of the present invention should be chosen to allow a fast dissolution of the active ingredients.

Two solid oral dosage forms are preferred, i.e. tablets and capsules.

Tablets

Especially with tablets, the choice of excipients is important. The excipients should allow a fast dissolution and on the other hand the excipients should allow a convenient industrial production of tablets with an appropriate aspect, an appropriate friability and sufficient hardness.

Tablets should have an appropriate hardness and friability mainly because said tablets need to be manufactured on an industrial scale at presses with high speed and said tablets have to be packed or filled of in all kinds of containers. If the tablet has an insufficient hardness or is rather friable the tablet that is taken by the patient may be broken or parts of the tablet may have crumbled into powder. As a consequence of this insufficient hardness or friability the patient can no longer be certain that he is taking in the correct amount.

The minimum required hardness of the tablets should be from about 1.5 daN (deca Newton) as measured by the test as described in the European Pharmacopoeia (3th Edition, 1997) on page 135, "resistance to crushing of tablets".

It should be noted that hardness, amongst other properties, of tablets is dependent upon the shape of the tablets.

Different shapes of tablets may be used according to the present invention. Tablets may be circular or oblate or oblong or any other shape that is known in the art. The tablets may be scored. It should be noted that also the shape of the tablets may for instance have an influence the disintegration rate.

The disintegration of tablets is measured according to the pharmaceutical technical procedure as described in the European Pharmacopoeia, third edition, (1997), page 127. The disintegration time of the present tablets should be less than about 30 minutes, interestingly less than 20 minutes and more interestingly less than about 15 minutes. The preferred tablets even have a disintegration time of less than about 3 minutes, even less than about 1.5 minutes.

The tablets of the present invention comprise tablet disintegrants, such as starch, pregelatinised starch, sodium starch glycolate (Explotab®), crosslinked povidone, crosslinked sodium carboxymethylcellulose, clays, microcrystalline cellulose (of the type available under the registered Trademark Avicel®), alginates, gums and others known in the art.

Tablets of the present invention preferably comprise as disintegrant crosslinked Carmellose Sodium (Carmellose Sodium is the British Approved Name of sodium carboxymethylcellulose, i.e. the sodium salt of a ether of cellulose, see Martindale, the Extra Pharmacopeia, 29th edition, page 1433). Said crosslinked Carmellose Sodium is referred to as Croscarmellose Sodium (USP NF, 1995 Edition, page 2238)

The disintegrant may be present in an amount of about 2% (w/w) to about 15% (w/w). An interesting range for the disintegrant is from about 3% (w/w) to about 10% (w/w). When percentages are used, these percentages are weight per weight (w/w) and represent the ratio (in percent) of the ingredient or the excipient based on the total weight of the tablet (or in the case of coated tablets of the tablet core). The "tablet core" is the tablet without the coating. When using a process wherein there is a granulation step, it may be advantageous to have disintegrant in the "internal phase" and in the "external phase". The term "internal phase" refers to the composition of the granules and the term "external phase" refers to the composition of the compression mixture. It was observed that tablets with disintegrants in the internal and the external phase showed a better disintegration and a better dissolution profile.

The tablet may further be formulated to include a variety of conventional excipients, depending on the exact formulation, such as binders, flavorings, buffers, diluents, colors, lubricants, sweetening agents, and glidants. Some excipients can serve multiple purposes.

Optionally, flavors may be incorporated in the composition, which may be chosen from synthetic flavor oils and flavoring aromatics and/or natural oils, extracts from plant leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so fort. The amount of flavor may depend on a number of factors including the organoleptic effect desired. Generally the flavor will be present in an amount from about 0.5% (w/w) to about 3.0% (w/w), when a flavor is used.

A variety of materials may be used as fillers or diluents. Examples are spray-dried or anhydrous lactose, sucrose, dextrose, mannitol, sorbitol, starch, cellulose (e.g. microcrystalline cellulose; Avicel), dihydrated or anhydrous dibasic calcium phosphate, and others known in the art. A tablet can comprise one single filler or diluent or a mixture of fillers or diluents. For instance, a mixture of lactose and micro crystalline cellulose can be used. Lactose is used as a pure diluent, while microcrystalline cellulose is a filler that has the property of yielding tablets with an appropriate hardness and it has disintegrant properties because cellulose fibers swell in contact with water.

A preferred form of lactose is lactose monohydrate DC which corresponds with Pharmatose DCL 11 that is commercially available from DMV International, The Netherlands, said lactose monohydrate DC is spray-dried lactose monohydrate.

Fillers or diluents may be present in a range from about 50% (w/w) to about 95% (w/w) based on the total weight of the tablet or tablet core. Interestingly the amount of fillers or diluents range from about 65% (w/w) to about 90% (w/w). Preferably, the amount of fillers or diluents range from about 66% (w/w) to about 86% (w/w). Interestingly, a spray-dried mixture of lactose monohydrate and microcrystalline cellulose in a ratio of about 75% by weight of lactose monohydrate and about 25% by weight of microcrystalline cellulose can be used. This mixture is commercially available under the registered tradename MICROCELAC®. This spray-dried mixture of lactose monohydrate and microcrystalline cellulose has the advantage that it will promote ordered mixing, which improves the content uniformity of the tablets. Indeed the solid oral dosage forms contain relatively small amounts of active ingredient in a large amount of filler. In such conditions content uniformity can pose problems, i.e. the tablets prepared in the same batch may not all have the same content of active ingredient due to segregation during manufacturing. In view of the fact that Regulatory Authorities often apply quite stringent rules for content uniformity of the solid oral dosage forms, batches with tablets not having a good content uniformity must be discarded. The spray-dried mixture of lactose monohydrate and microcrystalline cellulose has a porous structure wherein the active ingredient cisapride-(L)-tartrate can be inserted, leading to ordered mixing and consequently a good content uniformity.

Said MICROCELAC® is present in an amount ranging from about 80% (w/w) to 95% (w/w) based on the total weight of the tablet or the tablet core in the case of film coated tablets. Preferably, the MICROCELAC® is present in an amount of about 87% (w/w).

Lubricants can also be employed in the manufacture of certain dosage forms, and will usually be employed when producing tablets. Examples of lubricants are magnesium stearate, stearic acid, sodium stearyl fumarate, magnesium lauryl sulfate, hydrogenated vegetable oil and others known in the art. Preferred lubricants are magnesium stearate and sodium stearyl fumarate.

Lubricants generally are present in an amount ranging from about 0.2% (w/w) to 7.0% (w/w) based on the total weight of the tablet or the tablet core in the case of film-coated tablets. Interestingly, lubricants are present in amounts ranging from about 0.5% (w/w) to about 3.0% (w/w). Preferably, lubricants are present in amounts ranging from about 0.9% (w/w) to about 1.25% (w/w).

Glidants are normally used in the manufacture of tablets and also capsules. Interesting glidants are calcium silicate, magnesium silicate, colloidal anhydrous silica or talc. Mixtures of glidants may also be used. Preferred glidant for the tablet core or the capsule of this invention is colloidal anhydrous silica. The type normally used is commercially available under the tradename Aerosil®. Glidants are normally present in an amount ranging from about 0.05% (w/w) to about 1% (w/w) based on the total weight of the tablet core content. The preferred amount of glidant is about 0.3%.

Binders may be acacia, alginic acid, carboxymethylcellulose (sodium), cellulose (microcrystalline), dextrin, ethylcellulose, gelatin, glucose (liquid), guar gum, hydroxypropyl cellulose, hydroxypropyl methylcellulose, methylcellulose, polyethylene oxide, povidone, starch (pregelatinized) or syrup. Interesting binders are the hydroxypropyl methylcelluloses, especially the low-viscosity hydroxypropyl methylcelluloses. Preferred binder is hydroxypropyl methylcellulose 2910 of which a 2% aqueous solution at 20° C. has a viscosity of 15 mPa.s Other excipients such as coloring agents and pigments may also be added to the tablets of the present invention. Coloring agents and pigments include titanium dioxide and/or dyes approved for use in food and pharmaceuticals. A coloring agent is an optional ingredient in the tablet of the present invention, but when used, the coloring agent will be present in an amount up to 3.5% (w/w) based on the total tablet weight or the tablet core in the case of film-coated tablets.

Preferably, the coloring agent is present in the coating of the tablet, where again the coloring agent may be present in an amount ranging from 0.01% (w/w) to about 10% (w/w)

based upon the total weight of the coating, an interesting range starts from about 0.20% (w/w) up to about 7.5% (w/w) based upon the total weight of the coating.

As known in the art, tablet blends may be dry-granulated or wet-granulated before tabletting. Unexpectedly, it was found that when using cisapride-(L)-tartrate it was possible to prepare tablets using direct compression techniques. When cisapride monohydrate would be used as an active ingredient the formulation requires a surfactant to obtain the necessary wettability of the cisapride monohydrate. However, in order to add a surfactant to a tablet formulation a wet-granulation step is required. Hence, as a further embodiment of the present invention there should be mentioned the fact that the tablets of the present invention can be prepared by direct compression, i.e. the "usual" wet-granulation step can be omitted. This causes a considerable cost reduction in the production of these tablets.

It was also found that tablets prepared via direct compression gave a better dissolution profile than analogous tablets prepared via a wet granulation step.

Tablets of the present invention may be film-coated to provide ease of swallowing, taste masking and an elegant appearance. Many polymeric film-coating materials are known in the art. Known film-coating agents are sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methyl cellulose phthalate, methacrylic acid copolymer, methylcellulose, polyethylene glycol, polyvinyl acetate phthalate, shellac, sucrose, titanium dioxide, wax, zein. A preferred film-coating material is hydroxypropyl methylcellulose (HPMC). HPMC may be obtained commercially.

Coating agents are normally present in an amount ranging from about 50% (w/w) to about 95% (w/w) based upon the total weight of the film coating. The interesting range is from about 50% (w/w) to about 65% (w/w).

Antiadhesives are normally used in the film coating process to avoid sticking effects during film formation and drying. The preferred antiadhesive for this purpose is talc. The antiadhesive and especially talc is present in the film coating in an amount of about 5% (w/w) to 15% (w/w) based upon the total weight of the coating.

Other ingredients of the filmcoating may be plasticizers, such as castor oil, diacetylated monoglycerides, dibutyl sebacate, diethyl phthalate, glycerin, polyethylene glycol, propylene glycol, triacetin, triethyl citrate. Also mixtures of plasticizers may be utilized. The type of plasticizer depends upon the type of coating agent. Preferred plasticizer according to the present invention is propylene glycol. Said plasticizer is normally present in an amount ranging from 5% (w/w) to 30 (w/w) based on total weight of the film coating. Interesting range of plasticizer is from about 12% (w/w) to about 16% (w/w) based on the total weight of the film coating. Preferred amount of propylene glycol according to the present invention is about 14% (w/w).

An opacifier like titianium dioxide may also be present in an amount ranging from about 10% (w/w) to about 20% (w/w) based on the total weight of the coating.

When coloured tablets are desired then the colour is normally applied in the coating. Consequently, colouring agents and pigments may be present in the film coating. Preferred colouring agents are ferric oxides, which can either be red, yellow, black or blends thereof.

Said film-coating process may be carried out utilizing spray-coating equipment well-known in the art. Typically the coating can be carried out in a perforated pan such as those manufactured under the tradename of Glatt® (for example Glatt Coater 750) AccelaCota® and HiCoater®.

The tablet ting process itself is otherwise standard and readily practised by forming a tablet from a desired blend or mixture of ingredients into the appropriate shape using a conventional tablet press. Pressures are used ranging from about 0.5 ton/cm$^2$ (corresponding to about 50 MPa) to about 2.0 ton/cm$^2$ (corresponding to about 200 MPa). Below the lower limit, the tablets formed will not show appropriate hardness and above the higher limit the tablets may be so hard that they do not dissolve any more. Preferred range is from about 1.1 ton/cm$^2$ (corresponding to about 110 MPa) to about 1.7 ton/cm$^2$ (corresponding to about 170 MPa).

Capsules

Capsules according to the present invention comprise, apart form the active ingredient, fillers, glidants, lubricants and disintegrants.

The same fillers, glidants and lubricants as described above for the tablets may be used in the capsules. Preferred filler is lactose. Preferred glidants are colloidal silicon dioxide and talc. Talc also provides the anti-adherent properties needed to handle the powders. Preferred lubricant is magnesium stearate. Maize starch can be used as a disintegrant, which is a necessary ingredient for the capsule content in the case the capsule filling equipment uses tamping. In capsule filling equipment using tamping, the capsule content is packed together in several consecutive strokes and at the last stroke the packed capsule content is delivered into the capsule.

Fillers are present in an amount ranging from about 60% (w/w) to about 90% (w/w) based upon the total weight of the capsule content. Preferably, the fillers are present in an amount ranging from about 70% (w/w) to about 80% (w/w) based upon the total weight of the capsule content. Preferably, the fillers are present in an amount of about 75% (w/w).

Glidants are present in an amount of about 4% (w/w) to 7% (w/w) based upon the total weight of the content of the capsule. Preferably, the glidants are present in an amount of about 6% (w/w) based upon the total weight of the content of the capsule.

The lubricant or lubricants are present in an amount ranging from about 0.5% (w/w) to about 2.0% (w/w). Preferably, the lubricant or lubricants are present in an amount of about 1.25% (w/w) based upon the total weight of the content of the capsule.

Capsules are normally prepared from gelatin, they may be soft or hard gelatin capsules.

The capsules are prepared in a conventional way. The filler, for instance lactose, is milled together with the active ingredient and sieved. The resulting mixture is added to a mixture of the remainder of the excipients and mixed in a planetary mixer until a homogenous mixture is obtained. This powder is filled off in the capsule using art-known (automatic) capsule filling equipment.

Use

An advantage of the present solid oral dosage form is that, even when the solid oral dosage form according to the present invention has not yet completely dissolved in the acid environment of the stomach and is passed through to the gut, where the environment is about neutral, i.e. much less acidic, then still the cisapride tartrate is able to dissolve quickly, which is not the case with cisapride monohydrate.

The pharmaceutical dosage form, subject of the present invention, is to be used as a medicine for treating gastrointestinal disorders, such as, gastroparesis, either idiopathic or associated with diabetic neuropathy, anorexia nervosa, after vagotomy or partial gastrectomy (the symptoms mainly consist of early satiety, anorexia, nausea and vomiting); symptoms of X-ray or endoscopy negative upper digestive discomfort, characterized by early satiety, postprandial fullness, inability to finish a normal sized meal, bloating, excessive belching, anorexia, nausea, vomiting or by ulcer-like complaints (epigastric burning or pain), gastro-esophageal reflux disorders, including the curative and maintenance treatment of oesophagitis; in babies: chronic and excessive regurgitation or vomiting, when positional and dietary measures have failed; intestinal pseudo-obstruction, associated with motility dysfunctions resulting in insufficient propulsive peristaltism and in stasis of gastric and intestinal contents; restoration of colonic propulsive motility as a long-term treatment of chronic constipation. Consequently, the present invention further provides for a method of treating gastrointestinal disorders, especially gastro-oesophagal reflux disease.

Due to the properties of the present tablets the use of cisapride-(L)-tartrate, cisapride-(D)-tartrate, cisapride sulfate, cisapride citrate for the manufacture of an oral dosage form without drugfood interaction for the treatment of gastrointestinal disorders is disclosed. Also the use of cisapride-(L)-tartrate, cisapride-(D)-tartrate, cisapride sulfate, cisapride citrate for the manufacture of a medicament for treating gastrointestinal disorders in patients taking medication that increases the pH of the stomach in general or for the manufacture of a medicament for treating gastrointestinal patients taking proton pump inhibitors, H2-inhibitors or antacids in particular is claimed.

The solid oral cisapride dosage forms disclosed and described above can be administered to a mammal, including man, in need of such treatment when the mammal has eaten, regardless of how recently and of nature and the quantity of the food, without exhibiting an adverse food effect. To this end, and as an additional feature of this invention, this invention provides a therapeutic package suitable for commercial sale, comprising a container, an oral dosage form of cisapride which does not exhibit an adverse food effect contained therein and associated with said package, written (i.e. printed) matter non-limited as to whether the dosage form can be taken with or without food. The written matter is of the type containing information and/or instructions for the physician, pharmacist or patient. The written material can be "non-limited as to whether the dosage form can be taken with or without food" by virtue of including no statement regarding whether or not the dosage form can be taken with or without food, i.e. the statement is silent with regard to food effects. Alternatively, the written material can be non-limited by containing one or more statements affirmatively informing the user (i.e. the patient, pharmacist, or physician) that the said oral dosage form can be taken by or administered to a patient regardless whether the patient has eaten or otherwise imbibed food (optionally, for example, also stating something like "without regard to the type or quantity of food"). The written material cannot contain limiting language with respect to food, e.g., "This dosage form can not be taken with food" or "This dosage form may only be given after the patient has fasted" or the like.

The container can be in any conventional shape or form as known in the art which is made of a pharmaceutically acceptable material, for example a paper or cardboard box, a glass or plastic bottle or jar, a re-sealable bag, or a blister pack with individual dosages for pressing out of the pack according to a therapeutic schedule. The container employed can depend on the exact dosage form involved.

In view of the fact that the present dosage form of cisapride can be taken in or administered to a patient independently from a meal, the dosage form can be administered "pro re nata". This means that the administration of the dosage form can be symptom driven. In other words the patient can take the present dosage form when the patient feels one of the symptoms which are associated with the gastrointestinal disorder he is suffering from. This greatly improves the patient compliance because instead of having to think about taking his medication at the meal, the patient can take in the medication when the symptoms appear.

Experimental Part

EXAMPLE 1

Tablet A

The following ingredients were intimately mixed in a planetary mixer: cisapride-(L)-tartrate (13.23 mg, 7.35% (w/w)), spray-dried mixture of lactose monohydrate (75%) and microcrystalline cellulose (25%) (MICROCELAC®) (157.23 mg, 87.35% (w/w)), croscarmellose sodium (7.2 mg, (4.00% (w/w)), colloidal anhydrous silica (0.54 mg, 0.3% (w/w)), magnesium stearate (1.8 mg, 1.00% (w/w)) and compressed in a tabletting machine (type Korsch or Courtoy RO 2EHS, with compression rate of 36000 tabl/h) preparing tablets of 180 mg.

The tablet prepared according to the example above comprises:

| | | |
|---|---|---|
| cisapride-(L)-tartrate | 13.23 mg | 7.35% (w/w) |
| MICROCELAC® | 157.23 mg | 87.35% (w/w) |
| croscarmellose sodium | 7.2 mg | 4.00% (w/w) |
| colloidal anhydrous silica | 0.54 mg | 0.3% (w/w) |
| magnesium stearate | 1.8 mg | 1.00% (w/w) |

EXAMPLE 2

Tablet B

The following ingredients were intimately mixed in a planetary mixer: cisapride-(L)-tartrate (13.23 mg, 7.35% (w/w)), lactose DC (116.57 mg, 64.76% (w/w)), microcrystalline cellulose (Avicel®) (38.86 mg, 21.59% (w/w)), croscarmellose sodium (7.2 mg, (4.00% (w/w)), colloidal anhydrous silica (0.54 mg, 0.3% (w/w)), sodium stearyl fumarate (3.6 mg, 2.00% (w/w)) and compressed in a tabletting machine (type Korsch or Courtoy RO 2EHS, with compression rate of 36000 tabl/h) preparing tablets of 180 mg.

| | | |
|---|---|---|
| cisapride-(L)-tartrate | 13.23 mg | 7.35% (w/w) |
| lactose DC | 116.57 mg | 64.76% (w/w) |
| microcrystalline cellulose | 38.86 mg | 21.59% (w/w) |
| croscarmellose sodium | 7.2 mg | 4.00% (w/w) |
| colloidal anhydrous silica | 0.54 mg | 0.3% (w/w) |
| sodium stearyl fumarate | 3.6 mg | 2.00% (w/w) |

EXAMPLE 3

Tablet C

In an analogous manner as described in Examples 1 and 2, tablets with the following composition were prepared:

| | | |
|---|---|---|
| cisapride-(L)-tartrate | 6.61 mg | 3.68% (w/w) |
| lactose | 123.18 mg | 68.44% (w/w) |

-continued

| | | |
|---|---|---|
| microcrystalline cellulose | 38.86 mg | 21.59% (w/w) |
| croscarmellose sodium | 7.2 mg | 4.00% (w/w) |
| colloidal anhydrous silica | 0.54 mg | 0.3% (w/w) |
| magnesium stearate | 1.8 mg | 1.00% (w/w) |

EXAMPLE 4

Tablet D

In an analogous manner as described in Examples 1 and 2, tablets with the following composition were prepared:

| | | |
|---|---|---|
| cisapride-(L)-tartrate- | 26.44 mg | 14.72% (w/w) |
| lactose | 103.34 mg | 58.39% (w/w) |
| microcrystalline cellulose | 38.86 mg | 21.59% (w/w) |
| croscarmellose sodium | 7.2 mg | 4.00% (w/w) |
| colloidal anhydrous silica | 0.54 mg | 0.30% (w/w) |
| magnesium stearate | 1.8 mg | 1.00% (w/w) |

EXAMPLE 5

Tablet E

In an analogous manner as described in Examples 1 and 2, tablets with the following composition were prepared:

| | | |
|---|---|---|
| cisapride-(L)-tartrate | 13.23 mg | 7.35% (w/w) |
| famotidine | 10.00 mg | 5.56% (w/w) |
| MICROCELAC ® | 147.23 mg | 87.35% (w/w) |
| croscarmellose sodium | 7.2 mg | 4.00% (w/w) |
| colloidal anhydrous silica | 0.54 mg | 0.30% (w/w) |
| magnesium stearate | 1.8 mg | 1.00% (w/w) |

In the combination formulations Simethicone or alpha-D-galactosidase may be added to each of the above formulations to provide anti-flatulent relief. The quantity of simethicone administered to a patient in need of treatment thereof may vary according to patient need, but may be, for example, the typical known dosage range to treat flatulence (20–40 mg per tablet) or may be increased as necessary. Generally, the amount of ADG that may be employed in the above formulations ranges from about 675 to about 2250 GAIU or may be increased as necessary.

EXAMPLE 6

Preparation of Film-coated Tablets Using the Wet-granulation Step for the Tablet Cores Tablet F 6a) Preparation of the Binder Solution 5.280 kg of purified water was transferred into a steam heated jacketed vessel and was heated to a temperature of about 80° C. The water was transferred into a stainless steel container of 25 l and 792 g HPMC 2910 15 mPa.s was dissolved while mixing for 5 minutes with a propeller mixer (150–500 rpm). Again 12.32 kg of water was added while mixing for 2 minutes. Subsequently the solution was de-aerated by mixing at a speed of 60–150 rpm for 10 minutes. The thus prepared binder solution is left standing for a minimum of 8 hours.

6b) Granulation 23.700 kg of Lactose monohydrate 200 mesh, 2.911 kg of cisapride-(L)-tartrate and 7.920 kg of unmodified maize starch were successively transferred into the product container of the fluidized bed granulator type GPCG 30. The fluid-bed process was started and the ingredients were mixed until the outlet-air temperature reaches about 28° C. (process parameters: general air pressure: 5 bar, air flow rate: from about 300 to 600 m$^3$/h, shaking time: 7 seconds, shaking time interval 35 seconds, temperature of the inlet air: from about 45° C. to about 55° C., temperature of the outlet air: from about 27° C. to about 29° C.)

The binder solution prepared as described under 6a) was sprayed unto the powder mixture (process parameter: air flow rate: from about 400 to about 1000 m$^3$/h, shaking time: about 7 seconds, shaking time interval: about 35 seconds, diameter of the nozzle: 1.8 mm, position of the nozzle: top, spraying pressure 3 bar, spraying rate: from about 200 to 300 g/min, temperature of the inlet air: from about 45° C. to about 60° C., temperature of the outlet air: from about 21° C. to about 24° C.) After the spraying homogeneously wetted granules were obtained.

The drying process started immediately after the spraying process. The drying process was continued until the outlet-air temperature reached about 38° C. (process parameters: air flow rate: from about 400 to 1000 m$^3$/h, shaking time: 7 seconds, shaking time interval 35 seconds, temperature of the inlet air: from about 70° C. to about 75° C., temperature of the outlet air: from about 37° C. to about 39° C.)

6c) Preparation of the Compression Mixture

The dried granules prepared as described under 6b) were passed through an oscillating sieving apparatus of the type Frewitt (mesh openings: 1 mm, wire thickness: 0.65 mm) together with 2.772 kg of microcrystalline cellulose, 1.188 kg croscarmellose sodium, 118 g colloidal anhydrous silica and 198 g of magnesium stearate. The sieved powder was collected in the bowl of the planetary mixer of the type Collette MP 90 (speed of mixing: mixing arm: 45 rpm and the plateau: 20 rpm) and was mixed during 5 minutes until a homogeneous mixture was obtained.

6d) Compression

The compression mixture prepared as described under 6c) was pressed to tablets using a Killian rotary tablet press. Biconvex, white circular tablets with a nominal weight of 180 mg were prepared in this way. These tablets were referred to as tablet core hereinabove.

6e) Preparing of the Coating Suspension 6.307 kg of purified water was warmed up in a steam heated jacketed vessel to a temperature ranging from about 70° C. to about 75° C. The water was transferred into a stainless steel vessel of 25 l and 880 g of HPMC 2910 5 mPa.s and 220 g propylene glycol were added while mixing in a propeller mixer (speed of mixing: from about 400 to about 600 rpm). This mixture is referred to as mixture A.

3.153 kg of purified water, 176 g talc, 264 g titanium dioxide and 33 g yellow ferric oxide were transferred in a stainless steel container of 10 l and were homogenized for 10 to 15 minutes using a Silverson 2LR homogenizer. This mixture is referred to as mixture B.

Mixture B was added to mixture A while mixing with a propeller mixer(speed of mixing: from about 200 to about 400 rpm). The total mixture was mixed during 120 minutes to further de-aerate the coating suspension.

6f) Coating the Tablets 11.033 kg of the coating suspension prepared as described under 6e) was transferred into a stainless steel container of 25 l. The tablets prepared as described under 6a) to 6d) were transferred into the coating apparatus GC 750 and warm up the tablets. (Process parameters: temperature of the inlet air: from about 80° C. to about 90° C., temperature of the outlet air after warming up: from about 47° C. to about 49° C. The coating suspension was sprayed unto the tablets using the following parameters: rotational speed of the pan: 8 to 10 rpm, temperature of the inlet air: from about 80° C. to 90° C., temperature of the outlet air: from about 46° C. to about 49° C., volume of the inlet air: from about 750 m³ to about 850 m³, process chamber pressure<100 mPa, spraying air pressure: from 2.5 to 3.5 bar, temperature of the coating suspension is room temperature, spraying rate: from 90 to 100 g/min.

After the spraying process was over, the tablets were kept rotating and were allowed to cool down until the outlet-air temperature reached 30° C.

The resulting film-coated tablets were circular (diameter=8 mm), concave and yellow film coated.

The tablets were filled of in polyethylene bottles and Perlen tristar blisters.

According to the above described preparation the following tablet was prepared:

Tablet Core of Tablet F

| ingredient | amount | % (w/w) versus tablet core |
|---|---|---|
| cisapride-(L)-tartrate | 13.23 mg | 7.35% (w/w) |
| lactose monohydrate 200 mesh(*1) | 107.73 mg | 59.85% (w/w) |
| unmodified maize starch | 36.00 mg | 20.00% (w/w) |
| HPMC 2910 15 mPa.s(*2) | 3.60 mg | 2.00% (w/w) |
| microcrystalline cellulose | 12.60 mg | 7.00% (w/w) |
| croscarmellose sodium | 5.40 mg | 3.00% (w/w) |
| colloidal anhydrous silica | 0.54 mg | 0.30% (w/w) |
| magnesium stearate | 0.90 mg | 0.50% (w/w) |
| total weight of the tablet core: | 180.00 mg | |

(*1) 200 mesh is an indication of the type of lactose monohydrate that is used.
(*2) HPMC means hydroxypropyl methylcellulose, the number "2910" refers to the type of hydroxypropyl methylcellulose that is used. The first two digits,"29", represent the approximate percentage of methoxylgroups and the third and fourth digit,"10" represents the approximate percentage of hydroxypropylgroups.

Film Coating of Tablet F

| ingredient | amount | % (w/w) versus coating |
|---|---|---|
| HPMC 2910 5mPa.s | 4.00 mg | 55.95% (w/w) |
| Propylene glycol | 1.00 mg | 13.99% (w/w) |
| Titanium dioxide (E171) | 1.20 mg | 16.78% (w/w) |
| Talc | 0.80 mg | 11.19% (w/w) |
| Yellow Ferric Oxide (E172/C177492) | 0.15 mg | 2.10% (w/w) |
| total weight of coating: | 7.15 mg | |

Also indicated is the viscosity (15 mPa.s) of a 2% aqueous solution measured at 20° C. This is an indication of the molecular weight of the HPMC that is used.

EXAMPLE 7

Tablet G

According to the method described under example 6 the following tablet was prepared:

| cisapride-(L)-tartrate | 26.46 mg | 12.03% |
|---|---|---|
| lactose monohydrate 200 mesh | 111.48 mg | 50.67% |
| unmodified maize starch | 44.00 mg | 20.00% |
| croscarmellose sodium (*) | 4.95 mg | 2.25% |
| HPMC 2910 15 mPa.s | 2.75 mg | 1.25% |
| microcrystalline cellulose | 11.00 mg | 5.00% |
| croscarmellose sodium (*) | 17.60 mg | 8.00% |
| colloidal anhydrous silica | 0.66 mg | 0.30% |
| magnesium stearate | 1.10 mg | 0.50% |
| total weight of the tablet: | 220.0 mg | |

(*) The fact that croscarmellose sodium is mentioned twice indicates that croscarmellose sodium is encompassed in the granulation mixture and in the compression mixture. Consequently, there is croscarmellose sodium present in the so-called internal phase (the granulate) and in the so-called external phase (the compression mixture). With croscarmellose sodium present in the "internal" and "external" phase, the dissolution profile of the thus prepared tablet is better than with the tablet wherein the croscarmellose sodium is present only in the "external" phase.

The tablet was coated as described under Example 6.

EXAMPLE 8

Tablet H

According to the method described under example 6 the following tablet was prepared:

| cisapride-(L)-tartrate | 26.46 mg | 12.03% |
|---|---|---|
| lactose monohydrate 200 mesh | 119.18 mg | 54.17% |
| unmodified maize starch | 44.00 mg | 20.00% |
| croscarmellose sodium (*) | 4.40 mg | 2.00% |
| HPMC 2910 15 mPa.s | 2.20 mg | 1.00% |
| microcrystalline cellulose | 4.40 mg | 2.00% |
| croscarmellose sodium (*) | 17.60 mg | 8.00% |
| colloidal anhydrous silica | 0.66 mg | 0.30% |
| magnesium stearate | 1.10 mg | 0.50% |
| total weight of the tablet: | 220.0 mg | |

(*) see remark of croscarmellose in external and internal phase as described under example 7.

The tablet was coated as described under Example 6.

EXAMPLE 9

Tablet I

Tablet Comprising Equivalent of 5 mg Cisapride Base

According to the method described under example 6 the following tablet was prepared:

| cisapride-(L)-tartrate | 6.62 mg | 6.62% |
|---|---|---|
| lactose monohydrate 200 mesh | 60.59 mg | 60.59% |
| unmodified maize starch | 20.00 mg | 20.00% |
| HPMC 2910 15 mPa.s | 2.00 mg | 2.00% |
| microcrystalline cellulose | 7.00 mg | 7.00% |
| croscarmellose sodium | 3.00 mg | 3.00% |
| colloidal anhydrous silica | 0.30 mg | 0.30% |
| magnesium stearate | 0.50 mg | 0.50% |
| total weight of the tablet core: | 100.0 mg | |
| HPMC 2910 5 mPa.s | 3.00 mg | 57.03% |
| propylene glycol | 0.75 mg | 14.26% |
| titanium dioxide | 0.90 mg | 17.11% |
| talc | 0.60 mg | 11.41% |
| yellow ferric oxide | 0.01 mg | 0.23% |
| total weight of coating | 5.26 mg | |

EXAMPLE 10

Tablet J

Tablet Comprising Equivalent of 10 mg Cisapride Base

According to the method described under example 6 the following tablet was prepared:

| cisapride-(L)-tartrate | 13.23 mg | 7.35% |
|---|---|---|
| lactose monohydrate 200 mesh | 107.73 mg | 59.85% |
| unmodified maize starch | 36.00 mg | 20.00% |

-continued

| | | |
|---|---|---|
| HPMC 2910 15 mPa.s | 3.60 mg | 2.00% |
| microcrystalline cellulose | 12.60 mg | 7.00% |
| croscarmellose sodium | 5.40 mg | 3.00% |
| colloidal anhydrous silica | 0.54 mg | 0.30% |
| magnesium stearate | 0.90 mg | 0.50% |
| total weight of the tablet core: | 180.00 mg | |
| HPMC 2910 5 mPa.s | 4.00 mg | 55.94% |
| propylene glycol | 1.00 mg | 13.99% |
| titanium dioxide | 1.20 mg | 16.78% |
| talc | 0.80 mg | 11.19% |
| yellow ferric oxide | 0.15 mg | 2.10% |
| total weight of coating | 7.15 mg | |

EXAMPLE 11

Tablet K

Tablet Comprising Equivalent of 20 mg of Cisapride Base

According to the method described under example 6 the following tablet was prepared:

| | | |
|---|---|---|
| cisapride-(L)-tartrate | 26.46 mg | 12.03% |
| lactose monohydrate 200 mesh | 121.38 mg | 55.17% |
| unmodified maize starch | 44.00 mg | 20.00% |
| HPMC 2910 15 mPa.s | 4.40 mg | 2.00% |
| microcrystalline cellulose | 15.40 mg | 7.00% |
| croscarmellose sodium | 6.60 mg | 3.00% |
| colloidal anhydrous silica | 0.66 mg | 0.30% |
| magnesium stearate | 1.10 mg | 0.50% |
| total weight of the tablet core: | 220.00 mg | |
| HPMC 2910 5 mPa.s | 6.00 mg | 52.86% |
| propylene glycol | 1.50 mg | 13.21% |
| titanium dioxide | 1.80 mg | 15.86% |
| talc | 1.20 mg | 10.57% |
| yellow ferric oxide | 0.85 mg | 7.49% |
| total weight of coating | 11.35 mg | |

EXAMPLE 12

Capsule A

| ingredient | amount | % (w/w) based on total weight of content |
|---|---|---|
| cisapride-(L)-tartrate | 6.62 mg | 4.14% |
| lactose 125 mesh | 61.00 mg | 38.13% |
| lactose 200 mesh | 60.98 mg | 38.11% |
| maize starch | 20.00 mg | 12.50% |
| talc | 9.00 mg | 5.60% |
| magnesium stearate | 2.00 mg | 1.25% |
| colloidal anhydrous silica (Aerosil ®) | 0.40 mg | 0.25% |
| total weight of the content of the capsule: | 160.00 mg | |

The powder is filled off in a capsule type number 4

EXAMPLE 13

Capsule B

| ingredient | amount | % (w/w) based on total weight of content |
|---|---|---|
| cisapride-(L)-tartrate | 13.23 mg | 6.01% |
| lactose 125 mesh | 82.00 mg | 37.27% |

-continued

| ingredient | amount | % (w/w) based on total weight of content |
|---|---|---|
| lactose 200 mesh | 81.57 mg | 37.08% |
| maize starch | 27.50 mg | 12.50% |
| talc | 12.40 mg | 5.64% |
| magnesium stearate | 2.75 mg | 1.25% |
| colloidal anhydrous silica (Aerosil ®) | 0.55 mg | 0.25% |
| total weight of the content of the capsule: | 220.00 mg | |

The powder is filled off in a capsule type number 2

The capsules as described above are prepared by mixing the ingredients in a planetary mixer and filling the powder of in the appropriate capsules.

EXAMPLE 14

Dissolution Experiments

The dissolution of tablets comprising cisapride-(L)-tartrate having the composition and prepared as described in Example 1 was compared with tablets comprising cisapride monohydrate instead of cisapride-(L)-tartrate (the rest of the composition and the preparation being the same) at different pH-values.

Experimental Method

The test tablet was brought in a glass container containing 900 ml of the specified buffer at a temperature of 37° C. The stirring is performed by a paddle at a rotational speed of 50 rpm (rotations per minute). This test is s set forth in USP test <711> in a USP-2 dissolution apparatus. This latter test is described in US Pharmacopeia XXII, pp 1578–1579.

| a) pH = ± 1.5 (HCl : 0.1 N) | | |
|---|---|---|
| time (minutes) | % dissolved cisapride-L-tartrate tablet | % dissolved cisapride monohydrate tablet |
| 0 | 0.00 | 0.00 |
| 5 | 82.79 | 80.36 |
| 15 | 89.33 | 94.06 |
| 30 | 91.35 | 94.91 |
| 45 | 92.12 | 94.59 |
| 60 | 91.95 | 94.27 | conclusion: the dissolution of cisapride tartrate and cisapride monohydrate is comparable in 0.1 N HCl (pH=±1.5).

| b) pH = 4.5 (USP-buffer) | | |
|---|---|---|
| time (minutes) | % dissolved cisapride-L-tartrate tablet | % dissolved cisapride monohydrate tablet |
| 0 | 0.00 | 0.00 |
| 5 | 84.56 | 54.03 |
| 15 | 97.31 | 88.78 |
| 30 | 97.54 | 97.88 |
| 45 | 97.15 | 98.24 |
| 60 | 96.89 | 97.94 | conclusion: the solution of cisapride-(L)-tartrate is clearly better than that of cisapride monohydrate at pH 4.5.

| time (minutes) | c) pH = 6.5 (USP-buffer) | |
| --- | --- | --- |
| | % dissolved cisapride-L-tartrate tablet | % dissolved cisapride monohydrate tablet |
| 0 | 0.00 | 0.00 |
| 5 | 63.10 | 4.93 |
| 15 | 72.24 | 7.73 |
| 30 | 73.16 | 10.31 |
| 45 | 74.23 | 12.00 |
| 60 | 73.79 | 13.33 | conclusion: the dissolution of cisapride tartrate is clearly superior to that of cisapride hydrate at pH=6.5.

EXAMPLE 15

Pharmacokinetic Example

In an open, four-way cross-over phase-I trial, a total of 12 subjects, 8 males and 4 females, were randomized to receive single doses of 10 mg cisapride as the tartrate salt and as the monohydrate with and without a standard breakfast.

All subjects were given the following 4 treatments:

Treatment A: a single intake of a cisapride-(L)-tartrate tablet, 2 hours before a standard breakfast, i.e. fasting conditions.

Treatment B: a single intake of a cisapride-(L)-tartrate tablet immediately after the standard breakfast.

Treatment C: a single intake of cisapride monohydrate tablet (regular Prepulsid tablet), 2 hours before a standard breakfast, i.e. fasting conditions.

Treatment D: a single intake of cisapride monohydrate tablet (regular Prepulsid tablet), after the standard breakfast.

A standard breakfast consists of four slices of bread, one slice of ham, one slice of cheese, butter, jelly and two cups of coffee or tea with if desired milk and/or sugar, was served. During treatments B and D, subjects first had their breakfast and took their trial medication immediately after finishing it. Thereafter, subjects could resume their usual diet.

The trial medication was taken with 100 ml water.

Blood samples were taken until 48 h post-dosing. The plasma concentrations of cisapride were determined by means of a validated HPLC method (limit of quantification=2 ng/ml).

Pharmacokinetic Analysis

Based on the individual plasma concentration-time data, using the actual sampling times, the following pharmacokinetic parameters of cisapride were determined after each of the four treatments:

Cmax—peak plasma concentration, determined by visual inspection of the data tmax—time to reach the peak plasma concentration, determined by visual inspection of the data.

AUClast—area under the plasma concentration-time curve from time 0 to the last time point (last quantifiable concentration, calculated by linear trapezoidal summation.

AUC∞—area under the plasma concentration-time extrapolated to infinity t½term—terminal half-life, defined as 0.693/Sz The relative bioavailability of cisapride was calculated as the ratios of the Cmax and the AUC in the various treatments Results No serious adverse effects were reported and no treatments were stopped due to adverse effects.

The pharmacokinetic results are summarized in the table below:

TABLE

| Parameter | treatment A | treatment B | treatment C | treatment D |
| --- | --- | --- | --- | --- |
| tmax, h | 1.4 ± 0.4 | 2.1 ± 0.7 | 1.7 ± 0.5 | 2.3 ± 0.6 |
| Cmax, ng/ml | 61.7 ± 16.7 | 65.6 ± 17.7 | 50.6 ± 18.4 | 65.4 ± 16.9 |
| t½term, h | 8.8 ± 2.9 | 8.3 ± 2.1 | 9.1 ± 2.8 | 7.3 ± 1.2 |
| AUClast, ng.h/ml | 533 ± 188 | 619 ± 221 | 454 ± 139 | 599 ± 152 |
| AUC ∞ ng.h/ml | 578 ± 203 | 662 ± 243 | 497 ± 143 | 638 ± 163 |

Discussion

The mean tmax of cisapride upon intake of the trial medication after an overnight fast was reached after 1.4±0.4 h (A: cisapride tartrate—fasting) and 1.7±0.5 h (cisapride monohydrate—fasting). The influence of a meal delayed tmax until 2.1±0.7 h (B: cisapride tartrate—after breakfast) and 2.3±0.6 h (D: cisapride monohydrate—after breakfast).

The mean peak plasma concentrations of cisapride averaged 61.7±16.7 ng/ml (fasting) and 65.6±17.7 ng/ml (after breakfast) for the tartrate salt and 50.6±18.4 ng/ml (fasting) and 65.4±16.9 ng/ml (after breakfast) for the regular marketed cisapride monohydrate.

Geometric mean Cmax ratios were 107%, (B versus A), 80% (C versus A), 133% (D versus C) and 100% (B versus D), with associated classical 90%-confidence intervals of 98%–116%, 74–87%. 122–145% and 92–109%. Geometric mean AUC∞ratios were 114%, (B versus A), 88% (C versus A), 129% (D versus C) and 101% (B versus D), with associated classical 90%-confidence intervals of 106–123%, 81–94%, 120–139% and 92–107%.

With respect to the total exposure (AUC∞) bioequivalence is demonstrated for the tartrate salt, comparing administration after a standard breakfast and while fasting (B versus A). When fasting, the relative bioavailability of the regular marketed tablet (C) versus the newly developed tartrate salt (A) is also within the criteria set for bioequivalence. Cisapride monohydrate administered after a breakfast (D) resulted in a 29% higher exposure and 33% higher peak levels of cisapride in comparison with the fasting conditions (D versus C). Both cisapride formulations are bioequivalent when taken when taken after a meal (D versus B)

From the results of this trial, comparing the bioavailability of the newly developed cisapride tartrate with the regular marketed monohydrate after a single intake and the effects of food thereupon, the following can be concluded:

Fed or fasting conditions have little influence on absorption, peak levels and total exposure of the newly developed cisapride tartrate.

The regular marketed cisapride monohydrate is subject of a 30% increased bioavailability in fed conditions.

When taken with a standard meal, cisapride tartrate and monohydrate are bioequivalent

We claim:

1. Method of treating a gastrointestinal disorder selected from the group consisting of gastro-oesophageal reflux disease, gastroparesis, symptoms of x-ray or endoscopy negative upper digestive discomfort, chronic and excessive regurgitation or vomiting, intestinal psuedo-obstruction and restoration of colonic propulsive motility by administering to a patient in need of said treatment an oral dosage form comprising an effective amount of cisapride-(L)-tartrate, which oral dosage form is administered without a drug food interaction.

2. Method of treating a gastrointestinal disorder selected from the group consisting of gastro-oesophageal reflux disease, gastroparesis, symptoms of x-ray or endoscopy negative upper digestive discomfort, chronic and excessive regurgitation or vomiting, intestinal psuedo-obstruction and restoration of colonic propulsive motility in a patient taking medication which increases the pH of the stomach by administering to said patients, an oral dosage form comprising an effective amount of cisapride-(L)-tartrate.

3. Method of treating a gastrointestinal disorder selected from the group consisting of gastro-oesophageal reflux disease, gastroparesis, symptoms of x-ray or endoscopy negative upper digestive discomfort, chronic and excessive regurgitation or vomiting, intestinal psuedo-obstruction and restoration of colonic propulsive motility in a patient taking a proton pump inhibitor, a $H_2$-inhibitor or an antacid by administering to said patients, an oral dosage form comprising an effective amount of cisapride-(L)-tartrate.

4. Method of treating a gastrointestinal disorder selected from the group consisting of gastro-oesophageal reflux disease, gastroparesis, symptoms of x-ray or endoscopy negative upper digestive discomfort, chronic and excessive regurgitation or vomiting, intestinal psuedo-obstruction and restoration of colonic propulsive motility by administering to a patient in need of said treatment an oral dosage form comprising an effective amount of cisparide-(L)-tartrate, which oral dosage form is administered independently from a meal.

5. Method of treating a gastrointestinal disorder selected from the group consisting of gastro-oesophageal reflux disease, gastroparesis, symptoms of x-ray or endoscopy negative upper digestive discomfort, chronic and excessive regurgitation or vomiting, intestinal psuedo-obstruction and restoration of colonic propulsive motility by administering to a patient in need of said treatment an oral dosage form comprising an effective amount of cisparide-(L)-tartrate, which oral dosage form is administered during a meal.

6. Method of treating a gastrointestinal disorder selected from the group consisting of gastro-oesophageal reflux disease, gastroparesis, symptoms of x-ray or endoscopy negative upper digestive discomfort, chronic and excessive regurgitation or vomiting, intestinal psuedo-obstruction and restoration of colonic propulsive motility by administering to a patient an oral dosage form comprising an effective amount of cisparide-(L)-tartrate, which oral dosage form is administered together with a proton pump inhibitor, a $H_2$ antagonist or an antacid.

7. Method of treating a gastrointestinal disorder selected from the group consisting of gastro-oesophageal reflux disease, gastroparesis, symptoms of x-ray or endoscopy negative upper digestive discomfort, chronic and excessive regurgitation or vomiting, intestinal psuedo-obstruction and restoration of colonic propulsive motility by administering to a patient in need of said treatment an oral dosage form comprising an effective amount of cisparide-(L)-tartrate, which oral dosage form is administered pro re nata.

8. A method according to claim 11, wherein the gastrointestinal disorder is gastro-oesophagal reflux disease.

9. A method according to claim 2, wherein the gastrointestinal disorder is gastro-oesophagal reflux disease.

10. A method according to claim 4, wherein the gastrointestinal disorder is gastro-oesophagal reflux disease.

11. A method according to claim 7, wherein the gastrointestinal disorder is gastro-oesophagal reflux disease.

* * * * *